United States Patent [19]

Achgill et al.

[11] Patent Number: 4,987,233

[45] Date of Patent: Jan. 22, 1991

[54] PROCESS FOR PREPARING HERBICIDAL UREAS AND INSECTICIDAL CARBAMATES AND CARBAMATE DERIVATIVES

[75] Inventors: Ralph K. Achgill; Laurence W. Call, both of Lafayette, Ind.

[73] Assignee: Eli Lilly and Company, Indianapolis, Ind.

[21] Appl. No.: 207,696

[22] Filed: Jun. 15, 1988

[51] Int. Cl.$^5$ ............ C07D 285/06; C07D 285/08; C07D 285/13; C07D 277/82

[52] U.S. Cl. ........................... 548/140; 548/127; 548/128; 548/163; 560/157

[58] Field of Search ............ 548/128, 127, 140, 163

[56] References Cited

U.S. PATENT DOCUMENTS

| | | | |
|---|---|---|---|
| 2,409,712 | 10/1946 | Schweitzer | 260/453 |
| 2,756,135 | 7/1956 | Searle | 71/2.5 |
| 2,834,799 | 5/1958 | Sowa | 260/463 |
| 2,903,478 | 9/1959 | Lambrech | 260/479 |
| 3,062,864 | 11/1962 | Ospenson et al. | 260/479 |
| 3,217,037 | 11/1965 | Payne et al. | 260/566 |
| 3,313,684 | 4/1967 | Schegk et al. | 167/30 |
| 3,336,186 | 8/1967 | Pelssker et al. | 167/30 |
| 3,474,170 | 10/1969 | Scharpf | 424/285 |
| 3,639,633 | 2/1972 | Buchannan | 424/327 |
| 3,658,870 | 4/1972 | Buchannan | 260/453 |
| 3,736,338 | 5/1973 | Gates et al. | 260/340.5 |
| 3,917,478 | 11/1975 | Moser et al. | 71/90 |
| 4,130,414 | 12/1978 | Arndt et al. | 71/90 |
| 4,174,398 | 11/1979 | Regel et al. | 424/270 |
| 4,175,081 | 11/1979 | Driscoll | 548/140 |
| 4,412,079 | 10/1983 | Cebalo et al. | 548/141 |
| 4,611,079 | 9/1986 | Merger et al. | 560/25 |

FOREIGN PATENT DOCUMENTS

| | | | |
|---|---|---|---|
| 217166 | 4/1987 | European Pat. Off. | 125/06 |
| 1254468 | 11/1971 | United Kingdom | 548/140 |
| 1265857 | 3/1972 | United Kingdom | 548/140 |

OTHER PUBLICATIONS

Sandler, Org. Funct. Group Prep., vol. 2, pp. 134–138 (1972).
Veigand–Hilgetag, *Test Methods in Organic Chemistry*, M. Khimia Publishers, p. 506 (1968).
*Chemical Engineering*, Nov. 10, 1986, at 27.
*Chemical Abstracts*, 59, 9885b (1963).

*Primary Examiner*—Robert Gerstl
*Attorney, Agent, or Firm*—Douglas J. Taylor; Leroy Whitaker

[57] ABSTRACT

The present invention provides a process for preparing herbicidal ureas and insecticidal carbamates and carbamate derivatives comprising reacting an amine, alcohol, or oxime nucleophile with a urea in an inert organic solvent.

16 Claims, No Drawings

PROCESS FOR PREPARING HERBICIDAL UREAS AND INSECTICIDAL CARBAMATES AND CARBAMATE DERIVATIVES

BACKGROUND OF THE INVENTION

Thiadiazolyl and benzothiazolylureas are taught as herbicides in patents such as U.S. Pat. Nos. 4,412,079 and 2,756,135 and British Patent No. 1,254,468. Carbamates and carbamate derivatives, such as carbamoyloximes, are taught as insecticides in patents such as U.S. Pat. Nos. 3,313,684, 2,903,478, 3,474,170, and 3,217,037. The preparation of these herbicidal and insecticidal compounds generally requires the use of rather dangerous reactants such as phosgene or an isocyanate such as methylisocyanate or the like. These reactants, especially the isocyanates, are well known as highly toxic substances, as evidenced by the recent industrial accident involving the release of methylisocyanate into the atmosphere, resulting in great injury and loss of human life.

An object of this invention is to provide a process for preparing herbicidal ureas and insecticidal carbamates and carbamate derivatives which obviates the need to use dangerous reactants such as an isocyanate or phosgene. Accordingly, the present invention provides a process for preparing herbicidal thiadiazolyl and benzothiazolylureas and insecticidal carbamates and carbamoyloximes by reacting a nucleophile, such as an amine, alcohol, or oxime, with a urea in an inert solvent.

SUMMARY OF THE INVENTION

This invention provides a process for preparing a compound of the formula $$A-\underset{\underset{}{\overset{\overset{O}{\|}}{C}}}{}-N\underset{R^1}{\overset{R}{\diagdown}}$$

wherein A is $$B-\underset{R^2}{\overset{}{N}}-,$$

W—O—, or G=N—O—;

B is

[structures shown]

W is

G is $$R^5-\underset{R^1}{\overset{R^1}{\underset{|}{C}}}-\underset{H}{\overset{}{C}}= \text{ or } R^5-\underset{R^6}{\overset{}{C}}=;$$

E is —O— or —C(R$^4$)$_2$—;
R is C$_1$-C$_7$ alkyl;
R$^1$ is H, C$_1$-C$_7$ alkyl, C$_3$-C$_7$ cycloalkyl, phenyl, or C$_1$-C$_4$ alkylphenyl;
R$_2$ is H, C$_1$-C$_7$ alkyl, C$_3$-C$_7$ cycloalkyl, C$_2$-C$_7$ alkenyl, C$_2$-C$_7$ alkynyl, or phenyl optionally substituted with Cl, Br, —NO$_2$, —CF$_3$, C$_1$-C$_4$ alkyl, C$_1$-C$_4$ alkoxy, or —N(C$_1$-C$_4$ alkyl)$_2$;
R$^3$ is H, F, Cl, Br, —CF$_3$, C$_1$-C$_7$ alkyl optionally substituted with F, Cl, or Br, —S(O)$_n$ C$_1$-C$_7$ alkyl, C$_1$-C$_7$ alkoxy, C$_3$-C$_7$ cycloalkyl optionally substituted with F, Cl, or Br, or phenyl optionally substituted with F, Cl, Br, —NO$_2$, —CF$_3$, or C$_1$-C$_4$ alkyl;
R$^4$ is H or C$_1$-C$_4$ alkyl;
R$^5$ is C$_1$-C$_7$ alkoxy or —S(O)$_n$ C$_1$-C$_7$ alkyl;
R$^6$ is C$_1$-C$_5$ alkyl optionally substituted with F, Cl, or Br, C$_3$-C$_5$ cycloalkyl, phenyl, or $$-\underset{}{\overset{\overset{O}{\|}}{C}}-N(C_1-C_4$$

alkyl)$_2$;
X is R$^3$, —N=CH—N(C$_1$-C$_4$ alkyl)$_2$,

[structure]

—N(C$_1$-C$_4$ alkyl)$_2$, or —N(C$_2$-C$_4$ alkenyl)$_2$;
Y is H or S(O)$_n$ C$_1$-C$_7$ alkyl;
Z is H, C$_1$-C$_4$ alkyl, Cl, F, Br, haloalkyl, —NO$_2$, —N(C$_1$-C$_4$ alkyl)$_2$, —C≡N, phenyl, —S(C$_1$-C$_4$ alkyl), or C$_1$-C$_4$ alkoxy;
n is 0, 1, or 2; and
m is 1, 2 or 3,
comprising reacting a nucleophile of the formula A-H, wherein A is as defined above, with a urea of the formula $$\underset{R^1}{\overset{R}{\diagdown}}N-\underset{}{\overset{\overset{O}{\|}}{C}}-N\underset{R^1}{\overset{R}{\diagdown}},$$

wherein each R is independently chosen from R as set forth above, and each R$^1$ is independently chosen from R$^1$ as set forth above, in an inert solvent.

A preferred group of compounds, wherein A is

which can be prepared by the present process are those wherein B is

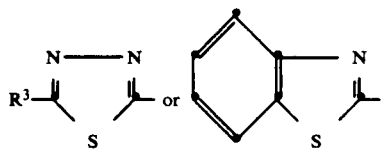

A more preferred group of compounds, wherein B is as above, which can be prepared by the present process are those wherein R is $C_1$–$C_4$ alkyl; $R^1$ is H or $C_1$–$C_4$ alkyl; $R^2$ is H, $C_1$–$C_4$ alkyl, or phenyl; and $R^3$ is H, —$CF_3$, or $C_1$–$C_4$ alkyl. The most preferred compounds, wherein B is as above, which can be prepared by the present process are 1-(5-[t-butyl]-1,3,4-thiadiazol-2-yl)-1,3-dimethylurea (generally known as tebuthiuron), 1-(5-trifluoromethyl-1,3,4-thiadiazol-2-yl)-1,3-dimethylurea (generally known as thiazfluron) and 1-benzothiazol-2-yl-1,3-dimethylurea (generally known as methabenzthiazuron). Tebuthiuron, thiazfluron and methabenzthiazuron are all commercial herbicides.

Another preferred group of compounds, wherein A is W—O—, which can be prepared by the present process are those wherein W is

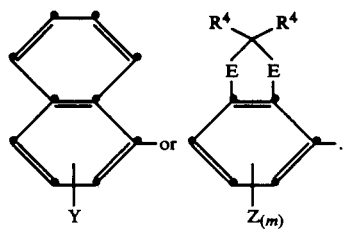

The most preferred compounds within this group which can be prepared by the present process are those wherein R is $C_1$–$C_4$ alkyl; $R^1$ is H or $C_1$–$C_4$ alkyl; $R^4$ is H or $C_1$–$C_4$ alkyl; one of E is —O— and the other is —$CH_2$—; and Y and Z are both H. The most preferred compounds, wherein W is above, which can be prepared by the present process are 1- naphthalenyl methylcarbamate (generally known as carbaryl) and 2,3-dihydro-2,2-dimethyl-7-benzofuranyl methycarbamate (generally known as carbofuran). Both carbaryl and carbofuran are commercial insecticides.

A preferred group of compounds, wherein A is G=N—O—, which can be prepared by the present process are those wherein G is

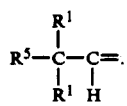

A more preferred group of compounds, wherein G is as above, which can be prepared by the present process are those wherein R is $C_1$–$C_4$ alkyl; $R^1$ is H or $C_1$–$C_4$ alkyl, and $R^5$ is —S($C_1$–$C_4$ alkyl). The most preferred compound, wherein G is as above, which can be prepared by the present process is 2-methyl-2-(methylthio)-propanal O-[(methylamino)carbonyl]oxime (generally known as aldicarb). Aldicarb is a commercial insecticide.

DETAILED DESCRIPTION OF THE INVENTION

The process of the present invention can be used to produce thiadiazolyl and benzothiazolylureas, such as those taught in references such as U.S. Pat. Nos. 4,412,079, 2,756,135, 4,130,414, 4,174,398, and 3,917,478, British Patent Nos. 1,254,468 and 1,195,672, and Belgian Patent No. 743,614, from amine starting materials. The process of the present invention can also be used to produce carbamates and carbamate derivatives, such as those taught in references such as U.S. Pat. Nos. 2,903,478, 3,062,864, 3,217,037, 3,313,684, 3,336,186, 3,474,170, 3,639,633, 3,658,870, and 3,736,338 and German Patent No. 1,145,162, from alcohol and oxime starting materials. The teaching of the above references with respect to the preparation of the amine, alcohol, or oxime starting materials, as well as the utility of the end-product ureas, carbamates, and carbamoyloximes, is hereby incorporated by reference.

It is believed that one skilled in the art of organic chemistry would be aware of the types of ureas, carbamates, and carbamoyloximes which can be prepared by the process of the present invention. However, the following specific compounds are mentioned in order to illustrate the type of herbicides and insecticides which can be produced by the process of this invention.

tebuthiuron
thiazfluron
benzthiazuron
methabenzthiazuron
carbofuran
allyxycarb
aminocarb
bendiocarb
carbaryl
dioxacarb
formetanate
methiocarb
3-(1-methylbutyl)phenyl methylcarbamate
3-(1-ethylpropyl)phenyl methylcarbamate
mexacarbate
promecarb
m-tolyl methylcarbamate
3,4-xylyl methylcarbamate
3,5-xylyl methylcarbamate
2-sec-butylphenyl methylcarbamate
terbucarb
aldicarb
methomyl
oxamyl All of the above are commercial herbicides or insecticides.

Certain of the compounds produced by the present process have substituents which may be optionally substituted with various groups as defined above. Optionally substituted, as used in this application, includes both mono- and poly-substitution, wherein each substituent is independently selected from the list of choices provided All of such substituted compounds are well known in the art.

The claimed process may be conducted by reacting a nucleophile with a urea in an inert solvent at a temperature of from about 100° C. to about 200° C. Inert solvents are those in which the reactants are substantially soluble and which do not undergo chemical reaction during the process. Examples of typical inert solvents which can be used include alkanes and cycloalkanes such as cycloheptane, octane, decane and the like; halogenated alkanes such as 1,1,2-trichloroethane, 1,2-bromoethane, bromoform and the like; ethers such as 1,3-dioxane, diethylene glycol dimethyl ether and the like; aromatic solvents such as toluene, chlorobenzene, the xylenes, cumene, o-dichlorobenzene and the like; and aromatic heterocyclic solvents such as pyridine, pyrrole, the picolines, the lutidines and the like. Preferred solvents employed in the process of the present invention are the aromatic solvents, especially the xylenes or cumene.

A nucleophile, as defined for purposes of the present invention, is an amine, alcohol, or oxime as defined by the formula A-H, wherein A is as previously delineated. The nucleophile starting materials are either commercially available, described in the literature in patents such as those cited previously, or can be prepared by methods known in the art. The concentration of nucleophile starting material in the solvent is not critical. In general, it is desirable to use as concentrated a solution as possible in order to minimize product loss during isolation. However, it is also desirable that enough solvent be used such that the product urea, carbamate, or carbamoyloxime remains in solution throughout the reaction.

The urea starting materials employed are either commercially available, known in the literature, or can be prepared by methods known in the art. The amount of urea employed is not critical so long as at least an equimolar amount relative to the nucleophile starting material is used. Generally, it is preferred that a slight molar excess of the urea be used, e.g., from about 1.1 molar equivalents to about 3.0 molar equivalents, with 1.5 molar equivalents being most preferred.

The urea starting materials employed are of the formula

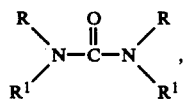

wherein each R and $R^1$ are independently chosen from the definition of R and $R^1$ set forth previously. Thus, the process of the invention can employ either a symmetrical or unsymmetrical urea as starting material. Examples of typical symmetrical or unsymmetrical ureas which can be employed in the process of the invention include such compounds as 1,3-dimethylurea, 1,3-diethylurea, 1,3-dipropylurea, 1,3-dimethyl-1,3-dipropylurea, 1,1-dipropyl-3-methylurea, 1,1-dibutyl-3-ethylurea, 1,3-dimethyl-1-cyclopentylurea, 1-methyl-1-methylphenyl-3-pentylurea, 1,3-diethyl-1-methyl-3-phenylurea, 1,1-dihexyl-3,3-diethylurea and 1-ethyl-1-phenyl-3-butyl-3-methylurea.

If a tetra-substituted unsymmetrical urea (i.e. none of the $R^1$ groups is H) is employed, the reaction product will be a mixture of two compounds. For example, if 1,1-dipropyl-3,3-dimethylurea is reacted with a nucleophile of the formula A-H the products produced will be

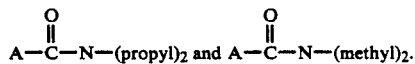

The desired product, for instance

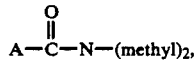

can then be isolated from the less desired compound by using standard isolation techniques such as distillation, crystallization and the like.

To avoid the yield loss and isolation problems associated with the quatro-substituted unsymmetrical ureas, a preferred process of the present invention uses either a tri-substituted unsymmetrical urea (one of the $R^1$ groups is H) or a symmetrical urea (both R groups the same, both $R^1$ groups the same) as starting material. It has been discovered that when a tri-substituted unsymmetrical urea is used as starting material, compounds of the formula

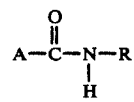

are preferentially produced relative to those of the formula

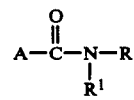

($R^1$ is not H). Thus, products of the formula

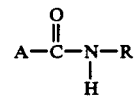

can be prepared in high yield and without expensive purification steps when tri-substituted unsymmetrical urea starting materials are employed.

Compounds of the formula

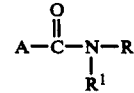

can also be prepared in high yield and without expensive purification steps using a symmetrical urea starting material. Symmetrical ureas are equally useful for preparing compounds where $R^1$ is H and compounds where $R^1$ is a substituent selected from the group consisting of $C_1$-$C_7$ alkyl, $C_3$-$C_7$ cycloalkyl, phenyl, or $C_1$-$C_4$ alkylphenyl, since either side of the urea molecule will produce the same final product. Processes of the present invention which use a symmetrical urea starting material to prepare urea, carbamate or carbamoyloxime final products are especially preferred.

An acid, while not required by the present process, can be employed to increase reaction between the nucleophile and the urea. Suitable acids which aid the present reaction include inorganic acids such as hydrochloric acid, hydrobromic acid and the like and organic acids such as methanesulfonic acid, p-toluenesulfonic acid and the like. Inorganic acids are preferred, especially hydrochloric acid, which can be used as either an anhydrous gas or as a concentrated aqueous solution. The amount of acid employed is not critical and will generally range from about 1.0 molar equivalents to about 3.0 molar equivalents relative to the nucleophile starting material. A preferred amount is about 1.5 molar equivalents.

If an organic or inorganic acid is to be employed in a process which requires an amine nucleophile starting material, a molar equivalent of the acid may be added by forming and isolating an acid addition salt of the amine starting material prior to use in the process of the invention. The isolated salt, mixed with a symmetrical or unsymmetrical urea in an inert solvent as described above for the non-salt compounds, provides both the required amine nucleophile starting material as well as one molar equivalent of acid. Additional acid may be added as desired if greater than an equimolar amount relative to the amine nucleophile is desired.

The process generally is conducted at reflux, for example at a temperature of about 100° C. to about 200° C. The process is substantially complete after about 1 to about 48 hours when conducted at the solvent's reflux temperature. The progress of the reaction can be followed, if desired, by standard high performance liquid chromatography (HPLC) analytical techniques in order to determine when the reaction is substantially complete.

Once the reaction is substantially complete, the urea, carbamate, or carbamoyloxime product can be isolated, if desired, by first cooling the solution to below 100° C. and adding water in order to remove unreacted urea starting material and any acid. The resulting aqueous layer may be separated from the organic layer, if desired, but need not be, and the resulting mixture cooled to about 0° C. The product compounds generally crystallize and can be isolated by standard filtration techniques in good purity and high yield.

The filtrate and the above described aqueous layer both often contain unreacted nucleophile starting material, as well as some urea, carbamate, or carbamoyloxime final product. These compounds can be recovered, if desired, by combining the filtrate and the aqueous layer and separating the resulting aqueous layer from the organic layer. The recovered organic layer is then combined with fresh solvent and additional nucleophile starting material, and the process of the present invention is repeated with the recycled material.

The following Examples illustrate specific aspects of the present invention. The Examples are not intended to limit the scope of the present process in any respect and should not be so construed.

Preparation 1

2-(t-Butyl)-5-methylamine-1,3,4-thiadiazole hydrochloride

To a one liter, 3-neck flask, with an agitator and a sub-surface gas addition system, were added 425 ml of a toluene solution which contained 250 g (1.46 mol) of 2-(t-butyl)-5-methylamine-1,3,4-thiadiazole. The solution was diluted by adding 325 ml of reagent grade toluene and heated to about 60° C. Anhydrous hydrochloric acid gas (60.0 g, 1.63 mol) was added at a rate sufficient to keep the solution temperature between 60° C. and 70° C. The resulting slurry was cooled to 0° C. and stirred for about 30 minutes at that temperature. The precipitated solid, recovered by filtration, was washed with 250 ml of toluene and dried overnight in a vacuum oven at 60° C. to provide 310.5 g (97.7% yield) of 2-(t-butyl)-5-methylamine-1,3,4-thiadiazole hydrochloride.

Preparation 2

1,1-Dipropyl-3-methylurea

To a 250 ml, 3-neck flask, with an agitator and condenser were added 22.0 g (0.25 mol) of 1,3-dimethylurea, 25.3 g (0.25 mol) of dipropylamine and 100 ml of cumene. The solution was heated at reflux (about 137° C.) for about 12 hours, cooled to 100° C., and the solvent was removed using vacuum distillation to provide a residue. The residue was dried in a vacuum oven at 60° C. to provide 41.5 g of 1,1-dipropyl-3-methylurea.

EXAMPLE 1

1-(5-[t-Butyl]-1,3,4-thiadiazole-2-yl)-1,3-dimethylurea

To a 250 ml, 3-neck flask, equipped with an agitator were added 34.4 g of 74.7% pure 2-(t-butyl)-5-methylamine-1,3,4-thiadiazole (0.15 moles of the amine), 30 ml of deionized water, 25 ml of xylenes (a reagent grade mixture of o, m, and p xylene), and 20.0 g of a 34.0% by weight hydrochloric acid solution (0.18 moles of hydrochloric acid). The mixture was heated to about 55° C., stirred for 15 minutes, and the organic layer separated from the aqueous layer.

The aqueous layer was mixed with 75 ml of xylenes. Sodium hydroxide (15.4 g of a 50% by weight sodium hydroxide solution) was added until the mixture's pH was about 8.0. The resulting two-phase solution was heated to about 50° C., stirred for 15 minutes, and the organic layer separated from the aqueous layer. The aqueous layer was extracted with an additional 30 ml of xylenes.

The organic extract was combined with the above organic layer and both solutions were added to a 250 ml, 3-neck flask, equipped with an agitator, condenser and a Dean Stark trap. The solution was dried by distilling an azeotropic mixture of water and xylenes until the solution's temperature reached about 145° C.

Once the solution was dried it was cooled to about 50° C. and 15.9 g (0.18 mol) of 1,3-dimethylurea were added. Anhydrous hydrochloric acid gas (6.6 g, 0.18 mol) was added sub-surface to the liquid. The resulting solution was heated until the xylenes solvent began to reflux (about 142° C.) and stirred at that temperature for 10 hours. After 10 hours the solution was cooled to about 70° C. and 30 ml of deionized water were added. The resulting two-phase mixture was stirred for 15 minutes and then the organic layer was separated from the aqueous layer.

The organic layer was mixed with 30 ml of deionized water and cooled to 0° C. After stirring for 1 hour at 0° C. the resulting slurry was filtered and the recovered crystals washed with 25 ml of deionized water. These crystals were dried in a vacuum oven at 60° C. to provide 24.6 g (70.1% yield) of 97.4% pure 1-(5-[t-butyl]-1,3,4-thiadiazol-2-yl)-1,3-dimethylurea. m.p. =161.0°–162.0° C.

The filtrate from the above filtration was combined with the reaction solution aqueous wash noted above and the pH of the resulting mixture was adjusted to 8.0 using a 50% by weight sodium hydroxide solution. The organic layer was separated from the aqueous layer and placed into a 100 ml volumetric flask. Additional xylenes solvent was added to the volumetric flask until the liquid volume reached 100 ml. One milliliter was withdrawn from the volumetric flask and mixed with acetonitrile until the resulting solution's volume was 100 ml. This solution was assayed by high performance liquid chromatography (HPLC) which disclosed that the filtrate and aqueous layers contained a total of 1.6 g of product and 2.9 g of unreacted amine starting material.

EXAMPLE 2

1-(5-[t-Butyl]-1,3,4-thiadiazole-2-yl)-1,3-dimethylurea

To a 250 ml, 3-neck flask, equipped with an agitator were added 34.4 g of 74.7% pure 2-(t-butyl)-5-methylamine-1,3,4-thiadiazole (0.15 moles of the amine), 40 ml of deionized water, and 75 ml of xylenes. The pH of the mixture was adjusted to about 8.0 by adding 1.6 g of a 50% by weight sodium hydroxide solution. The basic two-phase solution was heated to about 50° C. and stirred at that temperature for 15 minutes. The aqueous layer was separated from the organic layer and extracted with an additional 30 ml of xylenes.

The extract was combined with the above organic layer and both were added to a 250 ml, 3-neck flask, equipped with an agitator, condenser, and a Dean Stark trap. The solution was dried by distilling an azeotropic mixture of water and xylenes as in Example 1.

Once the solution was dried it was cooled to about 50° C. and 15.9 g (0.18 mol) of 1,3-dimethylurea were added. Anhydrous hydrochloric acid gas (6.6 g, 0.18 mol) was added sub-surface to the liquid. The resulting solution was reacted and washed according to the procedure described in Example 1. The organic layer, mixed with water, cooled, filtered, and dried in an analogous manner to the organic layer described in Example 1, provided 20.3 g (58.2% yield) of 98.0% pure 1-(5-t-butyl]-1,3,4-thiadiazol-2-yl)-1,3-dimethylurea. m.p.=161.0°-162.0° C.

The filtrate and the reaction solution aqueous wash were combined and the pH of the resulting mixture was adjusted to 8.0 using a 50% by weight sodium hydroxide solution. The resulting organic layer was separated and diluted according to the procedure of Example 1. High performance liquid chromatography (HPLC) assay of the final solution disclosed that the filtrate and aqueous layers contained a total of 2.2 g of product and 4.2 g of unreacted starting material.

EXAMPLE 3

1-(5-[t-Butyl]-1,3,4-thiadiazole-2-yl)-1,3-dimethylurea

To a 500 ml, 3-neck flask, equipped with an agitator and a condenser were added 31.0 g (0.15 mol) of 2-(t-butyl)-5-methylamine-1,3,4-thiadiazole hydrochloride prepared according to the procedure of Preparation 1, 20.0 g (0.23 mol) of 1,3-dimethylurea, and 75 ml of cumene. Additional hydrochloric acid was added by introducing anhydrous hydrochloric acid gas (3.0 g, 0.08 mol) sub-surface to the liquid. The resulting solution was heated until the solvent began to reflux (about 150° C.) and stirred at that temperature for about 6 hours. After 6 hours the solution was cooled to 80° C. and 30 ml of deionized water were added. The resulting two-phase mixture was stirred for 15 minutes and then the organic layer separated from the aqueous layer.

The organic layer was mixed with 30 ml of deionized water and cooled to 0° C. After stirring the mixture for 30 minutes at a temperature of about 0° C. the resulting slurry was filtered and the recovered crystals washed with 30 ml of deionized water. This material, dried in a vacuum oven at 60° C., provided 28.8 g (83.5% yield) of 99.2% pure 1-(5-[t-butyl]1,3,4-thiadiazol-2-yl)-1,3-dimethylurea. m.p.=160.8°-163.6° C.

The filtrate and the aqueous layer from above were combined and the resulting mixture treated according to the procedures described in Example 1. HPLC assay of the dilute solution indicated that the mixture contained 1.2 g of product and 1.8 g of unreacted starting material.

EXAMPLE 4

1-(5-[t-Butyl]-1,3,4-thiadiazole-2-yl)-1,3-dimethylurea

The procedure of Example 3 was repeated with the exception that the reaction solution was heated until the solvent began to reflux and stirred at that temperature for about 4 hours. This reaction time provided 28.3 g (82.4% yield) of a 99.6% pure 1-(5-t-butyl]-1,3,4-thiadiazol-2-yl)-1,3-dimethylurea product (m.p. 160.6°-162.8° C.) and a filtrate/aqueous layer mixture which contained 1.1 g of product and 1.8 g of unreacted starting material.

EXAMPLE 5

1-(5-[t-Butyl]-1,3,4-thiadiazole-2-yl)-1,3-dimethylurea

To a 250 ml, 3-neck flask, equipped with an agitator, a condenser, and a Dean Stark trap were added 36.4 g (0.17 mol) of 2-(t-butyl)-5-methylamine-1,3,4-thiadiazole hydrochloride prepared according to the procedure of Preparation 1, 29.4 g (0.33 mol) of 1,3-dimethylurea, and 90 ml of xylenes. Seventeen grams of a 38.0% by weight aqueous hydrochloric acid solution (0.17 moles of hydrochloric acid) were added. The resulting mixture was dried by distilling an azeotropic mixture of xylenes and water until the solution's temperature reached about 135° C.

Once the solution was dried the solvent was refluxed rather than removed and the solution was stirred at the reflux temperature for about 16 hours. The solution was then cooled to about 75° C. and 25 ml of deionized water were added. The resulting two-phase mixture was stirred for 15 minutes and the organic layer separated from the aqueous layer. Deionized water (25 ml) was used to wash the organic phase a second time.

The organic layer was separated from the second aqueous wash layer and 25 ml of deionized water were added. The mixture was cooled to about 0° C. and stirred at that temperature for 30 minutes. The resulting slurry was filtered and the recovered product was washed with 40 ml of deionized water and dried in a vacuum oven at 60° C. to provide 27.6 g (71.6% yield) of 98.6% pure 1-(5-[t-butyl]-1,3,4-thiadiazol-2-yl)-1,3-dimethylurea. m.p. 161.0°-162.8° C.

The filtrate and aqueous layers from above were combined and the resulting mixture treated according to the procedures of Example 1. HPLC assay of the dilute solution indicated that the mixture contained 2.0 g of product urea and 1.8 g of unreacted starting material.

EXAMPLE 6

1-(5-[t-Butyl]-1,3,4-thiadiazole-2-yl)-1,3-dimethylurea

The procedure of Example 1 was repeated with the exceptions that methanesulfonic acid (15.4 g of Aldrich reagent grade 98.0% by weight methanesulfonic acid solution, 0.16 mol of acid) was used in place of hydrochloric acid and the solution was heated until the solvent began to reflux and stirred at that temperature for five hours. This process provided 18.9 g (53.8% yield) of a 97.4% pure 1-(5-[t-butyl]-1,3,4-thiadiazole-2-yl)-1,3-dimethylurea product (m.p. 161.0°-162.6° C.) and a filtrate/aqueous layer mixture which contained 3.5 g of product and 5.4 g of unreacted starting compound.

EXAMPLE 7

1-(5-[t-Butyl]-1,3,4-thiadiazole-2-yl)-1,3-dimethylurea

To a 250 ml, 3-neck flask, equipped with an agitator and a condenser were added 35.0 g (0.17 mol) of 2-(t-butyl)-5-methylamine-1,3,4-thiadiazole hydrochloride prepared according to the procedure of Preparation 1, 16.2 g (0.18 mol) of 1,3-dimethylurea, 100 ml of xylenes, and 16.8 g (0.17 mol) of triethylamine. Anhydrous hydrochloric acid gas (7.4 g, 0.20 mol) was added sub-surface to the liquid at a rate which kept the liquid temperature below 70° C. The resulting solution was heated until the solvent began to reflux (about 142° C.) and stirred at that temperature for 10 hours. After 10 hours the solution was cooled to 80° C. and 25 ml of deionized water were added. The resulting two-phase mixture was stirred for 15 minutes and the organic layer separated from the aqueous layer.

The organic layer was mixed with 25 ml of deionized water and cooled to about 0° C., then stirred at that temperature for 30 minutes. The resulting slurry was filtered and the recovered crystals washed with 30 ml of water then dried in a vacuum oven at 60° C. to provide 25.3 g (66.5% yield) of 99.4% pure 1-(5-[t-butyl]-1,3,4-thiadiazole-2-yl)-1,3-dimethylurea. m.p. 161.0°-162.4° C.

The filtrate and aqueous layer above were combined and the resulting mixture was treated according to the procedures described in Example 1. HPLC assay of the dilute solution disclosed that the mixture contained 2.9 g of urea product and 5.4 g of unreacted starting material.

EXAMPLE 8

1-(5-[t-Butyl]-1,3,4-thiadiazole-2-yl)-1,3-dimethylurea

The title compound was prepared from 1,1-dipropyl-3-methylurea in the following manner. 1,1-Dipropyl-3-methylurea was prepared by adding 150 ml of cumene and 25.3 g (0.25 mol) of dipropylamine to a 250 ml, 3-neck flask, equipped with an agitator and a dropping funnel. Methylisocyanate (16.0 g, 0.28 mol) was added at a rate such that the temperature of the contents of the flask remained below 60° C. Once methylisocyanate addition was complete, the resulting solution was heated to about 60° C. and stirred at that temperature for 30 minutes. The solution was then heated to reflux (150° C.) and a total of 20 ml of cumene were distilled to remove the unreacted methylisocyanate.

The reaction mixture was then cooled to about 100° C. and 51.9 g (0.25 mol) of 2-(t-butyl)-5-methylamine-1,3,4-thiadiazole hydrochloride (prepared according to the procedure of Preparation 1) were added. The resulting solution was heated to reflux (about 154° C.) for abou 2 hours, cooled to 85° C., and diluted by the addition of 50 ml of deionized water were added. The resulting two-phase mixture was stirred for 30 minutes at 80° C., and then the organic layer separated from the aqueous layer.

The organic layer was mixed with 50 ml of fresh deionized water, cooled to about 0° C., and stirred at that temperature for 30 minutes. The resulting slurry was filtered and the recovered crystals washed with 50 ml of water, then dried in a vacuum oven at 60° C. to provide 43.8 g (75.5% yield) of 98.2% pure 1-(5-[t-butyl]-1,3,4-thiadiazole-2-yl)-1,3-dimethylurea. mp=160.4°-162.4° C. The product was identified by n.m.r. analysis (60 mHz, CZCl$_3$): $\delta$=1.55 (singlet, 9H); 3.10 (doublet, 3H); 3.65 (singlet, 3H); 8.05 (broad singlet, 1H).

The filtrate and aqueous layer above were combined and the resulting mixture treated according to the procedures described in Example 1. HPLC assay of the dilute solution disclosed that the mixture contained 2.4 g of urea product and 3.8 g of unreacted starting material.

EXAMPLE 9

1-(5-[t-butyl]-1,3,4-thiadiazole-2-yl)-1-methyl-3-ethylurea

To a 250 ml, 3-neck flask, equipped with an agitator and a condenser were added 21.0 g (0.10 mol) of 2-(t-butyl)-5-methylamine-1,3,4-thiadiazole hydrochloride, 13.9 g (0.14 mol) of 1,3-diethylurea, and 60 ml of cumene. Additional hydrochloric acid was added by introducing anhydrous hydrochloric acid gas (1.8 g, 0.05 mol) sub-surface to the liquid. The resulting solution was heated to reflux (about 150° C.) and stirred at that temperature for about 6 hours. After 6 hours the solution was cooled to 85° C. and diluted with 30 ml of deionized water. The resulting two-phase mixture was stirred for 30 minutes at 80° C. and then the organic layer separated from the aqueous layer.

The organic layer was mixed with 30 ml of deionized water and the pH of the resulting mixture was lowered to about 1.0 by adding a few drops of concentrated hydrochloric acid (38% by weight hydrochloric acid in water), while stirring. Again, the organic layer was separated from the aqueous layer. The organic layer was concentrated to an oily residue under reduced pressure. The oily product, stored in a vacuum oven at 70° C. overnight, was cooled to room temperature (22° C.) and allowed to solidify over the next three days to provide 12.1 g of solid product. The solid product was identified as 1-(5-[t-butyl]-1,3,4-thiadiazole-2-yl)-1-methyl-3-ethylurea by comparing n.m.r. spectra with a 1-(5-[t-butyl]-1,3,4-thiadiazole-2-yl)-1-methyl-3-ethylurea reference standard. The n.m.r. analyses were conducted on a 60 mHz instrument in CDCl$_3$: $\delta$=1.25 (triplet, 3H); 1.50 (singlet, 1H); 3.65 (singlet, 3H); 7.20 (triplet, 2H); 7.75-8.20 (broad triplet, 1H).

EXAMPLE 10

1-Naphthalenyl methylcarbamate

To a 500 ml, 3-necked flask, equipped with an agitator and a condenser were added 36.0 g (0.25 mol) of 1-naphthol, 35.2 g (0.40 mol) of 1,3-dimethylurea, 150 ml of cumene, and 38.4 g (0.40 mol of acid) of a 98% by weight methanesulfonic acid solution (Aldrich, reagent grade). The resulting solution was heated to reflux (about 154° C.) and stirred at that temperature for about 6 hours. After 6 hours the solution was cooled to 90° C. and diluted with 100 ml of deionized water. The resulting two-phase mixture was stirred for 15 minutes at about 80° C., and then the organic layer separated from the aqueous layer.

The organic layer was mixed with 50 ml of deionized water and cooled to 0° C. After stirring the mixture for 30 minutes at a temperature of about 0° C. the resulting slurry was filtered and the recovered crystals washed with 25 ml of deionized water, followed by 20 ml of cold (5° C.) cumene. The crystals were dried in a vacuum oven at 60° C. to provide 11.3 g of title product.

The above product was purified by dissolving it in 50 ml of hot (90° C.) toluene. Once all product had dissolved, the solution was cooled to 0° C. and stirred for 30 minutes at that temperature. The resulting slurry was filtered and the recovered crystals washed with 30 ml of toluene. This material, dried in a vacuum oven at 60° C., provided 10.1 g of 1-naphthalenyl methylcarbamate. m.p.=139°–140° C. The product was identified as 1-naphthalenyl methylcarbamate by comparing n.m.r. spectra with a 1-naphthalenyl methylcarbamate reference standard. The n.m.r. analyses were conducted on a 60 mHz instrument in $CDCl_3$: $\delta$=2.75 (doublet, 3H); 5.45 (singlet, 1H); 7.25–8.20 (broad multiplet, 7H).

EXAMPLE 11

1-Benzothiazol-2-yl-1,3-dimethylurea

To a 250 ml, 3-neck flask, equipped with an agitator, a condenser, and a sub-surface gas addition system were added 16.4 g (0.10 mol) of 2-methylaminobenzothiazole, 13.2 g (0.15 mol) of 1,3-dimethylurea and 100 ml of cumene. Anhydrous hydrochloric acid gas (5.5 g, 0.15 mol) was added sub-surface to the liquid at a rate which kept the liquid temperature below 90° C. The resulting solution was heated to reflux (about 150° C.) and stirred at that temperature for about 6 hours. After 6 hours the solution was cooled to about 90° C. and 50 ml of deionized water were added. The resulting two-phase mixture was stirred for 30 minutes at about 80° C. and then the organic layer was separated from the aqueous layer.

The organic layer was mixed with 50 ml of deionized water and the resulting two-phase mixture heated to about 80° C. Several drops of a 50% sodium hydroxide solution were added in order to increase the pH of the aqueous layer to about 11.0. The basic mixture was stirred for an additional five minutes and then the organic layer was again separated from the aqueous layer.

The organic layer was mixed, once more, with 50 ml of deionized water and the resulting mixture cooled to about 0° C. After stirring the mixture for 30 minutes at a temperature of about 0° C. the resulting slurry was filtered and the recovered crystals washed with 25 ml of deionized water. This material, dried in a vacuum oven at 60° C., provided 12.2 g (55.2% yield) of 1-benzothiazol-2-yl-1,3-dimethylurea. mp=120°–121° C. The product was identified as 1-benzothiazol-2-yl-1,3-dimethylurea by comparing n.m.r. spectra with a 1-benzothiazol-2-yl-1,3-dimethylurea reference standard. The n.m.r. analyses were conducted on a 60 mHz instrument in $CDCl_3$:$\delta$=3.10 (doublet, 3H); 3.60 (singlet, 3H); 7.25–7.65 (broad multiplet, 4H); 7.80 (doublet, 1H).

EXAMPLE 12

2,3-Dihydro-2,2-dimethyl-7-benzofuranyl methylcarbamate

To a 500 ml, 3-neck flask, equipped with an agitator, a condenser, and a sub-surface gas addition system were added 41.1 g (0.25 mol) of 2,3-dihydro-2,2-dimethylbenzofuran-7-ol, 35.2 g (0.40 mol) of 1,3-dimethylurea, and 180 ml of cumene. The solution was heated to reflux (about 156° C.) and a total of 30 ml of cumene were removed by distillation in order to remove a small amount of water present in the reaction flask. Anhydrous hydrochloric acid gas (14.6 g, 0.40 mol) was added sub-surface to the liquid over a three hour period while refluxing the solution. After hydrochloric acid addition, the resulting solution was stirred at the reflux temperature for 8 hours, then cooled to about 80° C. Deionized water (50 ml) was added. The resulting two-phase mixture was stirred for 15 minutes at about 80° C. and then the organic layer was separated from the aqueous layer.

The organic layer was mixed with 50 ml of deionized water and the resulting two-phase mixture heated to about 80° C. The mixture was stirred for about 15 minutes at 80° C. and then the organic layer was again separated from the aqueous layer.

The organic layer was mixed, once more, with 25 ml of deionized water and the resulting mixture cooled to about 0° C. After stirring for one hour at a temperature of about 0° C. the resulting slurry was filtered and the recovered crystals washed with 25 ml of deionized water, followed by 10 ml of chilled (0° C.) cumene. These crystals, dried in a vacuum oven at 50° C., provided 15.5 g of 2,3-dihydro-2,2-dimethyl-7-benzo?furanyl methylcarbamate. m.p.=148.0°–150.0° C.

Further product was isolated from the filtrate as follows. The organic layer of the filtrate was separated from the aqueous layer and the organic solvent removed by vacuum distillation to provide an oily residue. Hexane (100 ml) was added to the residue. Cumene (75 ml) was added slowly until the oily residue dissolved in the hexane/cumene solution. The solution was cooled to about 0° C. and 25 ml of deionized water were added. The resulting two-phase mixture was stirred for one hour at about 0° C. and the resulting slurry was filtered. The recovered crystals were washed with 20 ml of deionized water, followed by 5 ml of hexane. These crystals, dried in a vacuum oven at 50° C., provided 2.8 g of 2,3-dihydro-2,2-dimethyl-7-benzofuranyl methylcarbamate. mp=146.0°–149.0° C.

The two products were combined to provide a total of 18.3 g (33.0% yield) of 2,3-dihydro-2,2-dimethyl-7-benzofuranyl methylcarbamate. The product was identified as title compound by comparing n.m.r. spectra with a 2,3-dihydro-2,2-dimethyl-7-benzofuranyl methylcarbamate reference standard. The n.m.r. analyses were conducted on a 60 mHz instrument in $CDCl_3$:$\delta$=1.45 (singlet, 6H); 2.85 (doublet, 3H); 3.10 (singlet, 2H); 5.25 (singlet, 1H); 6.90 (broad multiplet, 3H).

EXAMPLE 13

2,3-Dihydro-2,2-dimethyl-7-benzofuranyl methylcarbamate

To a 250 ml, 3-neck flask, equipped with an agitator, a condenser, and a dropping funnel were added 100 ml of cumene and 11.1 g (0.11 mol) of dipropylamine. Methylisocyanate (7.5 g, 0.13 mol) was added at a rate such that the temperature of the contents of the flask remained below 60° C. Once methylisocyanate addition was complete, the resulting solution was heated to refux (about 150° C.) and a total of 10 ml of cumene were distilled in order to remove unreacted methylisocyanate.

Following removal of the unreacted methylisocyanate and the 10 ml of cumene, the remaining solution was cooled to about 80° C. and 16.4 g (0.10 mol) of 2,3-dihydro-2,2-dimethylbenzofuran-7-ol were added. Anhydrous hydrochloric acid gas (4.0 g, 0.11 mol) was added sub-surface to the liquid. After hydrochloric acid addition, the resulting solution was heated to reflux (about 154° C.) and stirred at that temperature for about 4 hours. The solution was then cooled to about 90° C. and 50 ml of deionized water were added. The resulting two-phase mixture was stirred for 30 minutes at about 80° C. and the organic layer was separated from the aqueous layer.

The organic layer was mixed with 25 ml of deionized water and cooled to about 0° C., then stirred at that temperature for 30 minutes. The resulting slurry was filtered and the recovered crystals washed with 25 ml of deionized water. The crystals were then dried in a vacuum oven at 60° C. to provide 12.3 g (55.7% yield) of 2,3-dihydro-2,2-dimethyl-7-benzofuranyl methylcarbamate. mp=151.0°-152.0° C.

EXAMPLE 14

2,3-Dihydro-2,2-dimethyl-7-benzofuranyl methylcarbamate

To a 250 ml, 3-neck flask, equipped with an agitator, a condenser, and a sub-surface gas addition system were added 16.4 g (0.10 mol) of 2,3-dihydro-2,2-dimethylbenzofuran-7-ol, 20.7 g (0.13 mol) of 1,1-dipropyl-3-methylurea (prepared according to the procedure of Preparation 2), and 100 ml of cumene. Anhydrous hydrochloric acid gas (4.6 g, 0.125 mol) was added subsurface to the liquid. The resulting solution was heated to about 115° C. and stirred at that temperature for about 16 hours. After 16 hours the solution was heated to reflux (about 155° C.) and stirred at that temperature for one hour. The solution was then cooled to about 80° C. and 50 ml of deionized water were added. The pH of the resulting two-phase mixture was increased to about 4.0 using a few drops of a 50% sodium hydroxide solution. After the pH was increased, the two-phase mixture was stirred for 30 minutes at about 80° C. and the organic layer was separated from the aqueous layer.

The organic layer was mixed with 25 ml of deionized water and cooled to about 0° C. After stirring the two-phase mixture for 30 minutes at a temperature of about 0° C. the resulting slurry was filtered and the recovered crystals washed with 20 ml of deionized water. These crystals, dried in a vacuum oven at 60° C., provided 13.4 g (60.6% yield) of 2,3-dihydro-2,2-dimethyl-7-benzofuranyl methylcarbamate. m.p.=151.0°-152.0° C.

EXAMPLE 15

2,3-Dihydro-2,2-dimethyl-7-benzofuranyl methylcarbamate

To a 250 ml, 3-neck flask, equipped with an agitator, a condenser, and a sub-surface gas addition system were added 11.0 g (0.125 mol) of 1,3-dimethylurea, 16.2 g (0.125 mol) of dibutylamine, and 100 ml of cumene. The solution was heated until the solvent began to reflux (about 151° C.). Heating was continued for about 6 hours while the solvent was refluxed and the monomethylamine generated during the reaction was allowed to escape.

When monomethylamine evolution appeared to cease, the solution was cooled to about 80° C. and 16.4 g (0.10 mol) of 2,3-dihydro-2,2-dimethylbenzofuran-7-ol were added. Anhydrous hydrochloric acid gas (4.6 g, 0.125 mol) was added sub-surface to the liquid at a rate such that the temperature of the contents of the flask remained about 80° C. The resulting solution was heated to about 115° C. and stirred at that temperature for 16 hours. After 16 hours the solution was heated to reflux (about 154° C.) and stirred at that temperature for one hour. The solution was then cooled to about 80° C. and 50 ml of deionized water were added. The pH of the resulting two-phase mixture was increased to about 4.0 using a few drops of a 50% sodium hydroxide solution. The two-phase mixture was then stirred for 30 minutes at about 80° C. and the organic layer was separated from the aqueous layer.

The organic layer was mixed with 25 ml of deionized water and cooled to about 0° C. After stirring the two-phase mixture for 30 minutes at a temperature of about 0° C. the resulting slurry was filtered and the recovered crystals washed with 20 ml of deionized water. These crystals, dried in a vacuum oven at 60° C., provided 11.6 g (52.5% yield) of 2,3-dihydro-2,2-dimethyl-7-benzofuranyl methylcarbamate. mp=151.0°-152.0° C.

EXAMPLE 16

3,5-Xylyl methylcarbamate

To a 250 ml, 3-neck flask, equipped with an agitator, a condenser, and a sub-surface gas addition system were added 12.1 g (0.10 mol) of 3,5-dimethylphenol, 14.1 g (0.16 mol) of 1,3-dimethylurea, and 75 ml of o-dichlorobenzene. The solution was heated to about 175° C. and 5.9 g (0.16 mol) of anhydrous hydrochloric acid gas were added sub-surface to the liquid at a rate such that the temperature of the content of the flask remained about 175° C. After hydrochloric acid addition, the solution was stirred for 6 hours at 175° C. and then cooled to about 80° C. Deionized water (25 ml) was added to the cooled solution and the resulting two-phase mixture was stirred for 15 minutes at about 80° C. The organic layer was then separated from the aqueous layer.

The organic layer was mixed with 25 ml of deionized water and the organic layer again was separated from the aqueous layer. The o-dichlorobenzene solvent was removed under reduced pressure to provide a residue, which was dissolved in 70 ml of a hot (70° C.) 1:1 cumene:hexane solution. The cumene/hexane solution was cooled to about 0° C. and stirred at that temperature for one hour. The resulting slurry was filtered and the isolated crystals washed with 20 ml of deionized water, followed by 10 ml of cold (0° C.) cumene. The crystals were then dried in a vacuum oven at 50° C. to provide 5.9 g (33.1% yield) of 3,5-xylyl methylcarbamate. m.p.=98.5°-99.5° C. The crystals were identified as 3,5-xylyl methylcarbamate by comparing n.m.r. spectra with a 3,5-xylyl methylcarbamate reference standard. The n.m.r. analyses were conducted on a 60 mHz instrument in CDCl$_3$:δ=2.3 (singlet, 6H); 2.85 (doublet, 3H); 5.15 (singlet, 1H); 6.85 (broad singlet, 3H).

We claim:

1. A process for preparing a compound of the formula

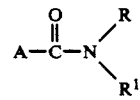

wherein
A is

B is

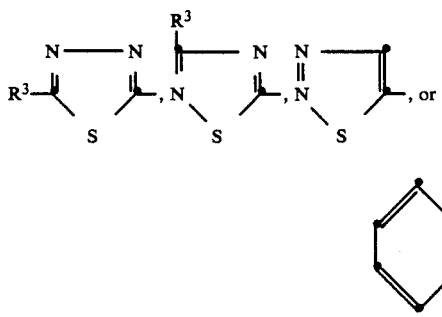

R is $C_1$-$C_7$ alkyl;

$R^1$ is H, $C_1$-$C_7$ alkyl, $C_3$-$C_7$ cycloalkyl, phenyl or $C_1$-$C_4$ alkylphenyl;

$R^2$ is $C_1$-$C_7$ alkyl, $C_3$-$C_7$ cycloalkyl, $C_2$-$C_7$ alkenyl, $C_2$-$C_7$ alkynyl, or phenyl optionally substituted with Cl, Br, —$NO_2$-$CF_3$, $C_1$-$C_4$ alkyl, $C_1$-$C_4$ alkoxy or —N($C_1$-$C_4$ alkyl)$_2$;

$R^3$ is H, F, Cl, Br, —$CF_3$, $C_1$-$C_7$ alkyl optionally substituted with F, Cl, or Br, —$S(O)_n$ $C_1$-$C_7$ alkyl, $C_1$-$C_7$ alkoxy, $C_3$-$C_7$ cycloalkyl optionally substituted with F, Cl, or Br, or phenyl optionally substituted with F, Cl, Br, —$NO_2$, —$CF_3$, or $C_1$-$C_4$ alkyl; and n is 0, 1 or 2;

comprising reacting a nucleophile of the formula A-H, wherein A is as defined above, with at least an equimolar amount of a urea of the formula

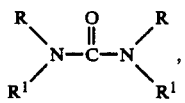

wherein each R is independently chosen from R as set forth above, and each $R^1$ is independently chosen from $R^1$ as set forth above, in an inert organic solvent at a temperature of from about 100° C. to about 200° C.

2. A process of claim 1 in which the urea is a tri-substituted un symmetrical urea wherein each R is independently $C_1$-$C_7$ alkyl, and one of $R^1$ is H and the other $R^1$ is $C_1$-$C_7$ alkyl, $C_3$-$C_7$ cycloalkyl, phenyl, or $C_1$-$C_4$ alkylphenyl.

3. A process of claim 1 in which the urea is a symmetrical urea wherein each R is the same and is $C_1$-$C_7$ alkyl, and each $R^1$ is the same and is H, $C_1$-$C_7$ alkyl, $C_3$-$C_7$ cycloalkyl, phenyl, or $C_1$-$C_4$ alkylphenyl.

4. A process of claim 1 wherein B is

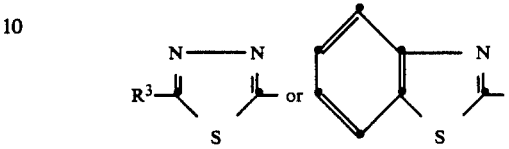

and R, $R^1$, $R^2$, $R^3$, and n are as defined above.

5. A process of claim 4 wherein R is $C_1$-$C_4$ alkyl; $R^1$ is H or $C_1$-$C_4$ alkyl; $R^2$ is $C_1$-$C_4$ alkyl, or phenyl; and $R^3$ is H, —$CF_3$, or $C_1$-$C_4$ alkyl.

6. A process of claim 5 wherein the product urea is 1-(5-1,3,4-thiadiazole-2-yl)-1,3-dimethylurea.

7. A process of claim 5 wherein the product urea is 1-(5-trifluoromethyl-1,3,4-thiadiazole-2-yl)-1,3-dimethylurea.

8. A process of claim 5 wherein the product urea is 1-benzothiazol-2-yl-1,3-dimethylurea.

9. A process of claim 1 in which the inert organic solvent is an aromatic solvent.

10. A process of claim 9 in which the aromatic solvent is xylene, a mixture of xylenes, or cumene.

11. A process of claim 1 in which an organic or inorganic acid is used to increase reaction between the nucleophile and the urea.

12. A process of claim 11 in which an inorganic acid is used to increase reaction between the nucleophile and the urea.

13. A process of claim 12 in which the inorganic acid is hydrochloric acid.

14. A process for preparing 1-(5-1,3,4-thiadiazole-2-yl)-1,3-dimethylurea comprising reacting 2-(t-butyl)-5-methylamine-1,3,4-thiadiazole with at least an equimolar amount of 1,3-dimethylurea in an inert aromatic solvent, at a temperature of from about 100° C. to about 200° C., using hydrochloric acid to increase reaction between the 2-(t-butyl)-5-methylamine-1,3,4-thiadiazole and the 1,3-dimethylurea.

15. The process of claim 14 in which the aromatic solvent is xylene or a mixture of xylenes.

16. The process of claim 14 in which the aromatic solvent is cumene.

* * * * *